(12) United States Patent
Yada et al.

(10) Patent No.: US 9,827,199 B2
(45) Date of Patent: Nov. 28, 2017

(54) HYDROMORPHONE HYDROCHLORIDE-CONTAINING ORAL SUSTAINED-RELEASE PHARMACEUTICAL COMPOSITION

(71) Applicant: Daiichi Sankyo Company, Limited, Chuo-ku, Tokyo (JP)

(72) Inventors: Shuichi Yada, Fujisawa (JP); Hideki Yano, Fujisawa (JP); Kazuhiro Yoshida, Setagaya-ku (JP); Sachiko Fukui, Kawasaki (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 14/635,813

(22) Filed: Mar. 2, 2015

(65) Prior Publication Data

US 2015/0231083 A1    Aug. 20, 2015

Related U.S. Application Data

(63) Continuation of application No. PCT/JP2013/073519, filed on Sep. 2, 2013.

(30) Foreign Application Priority Data

Sep. 3, 2012   (JP) ................................ 2012-192783

(51) Int. Cl.
*A61K 9/20* (2006.01)
*A61K 31/485* (2006.01)

(52) U.S. Cl.
CPC .......... *A61K 9/2054* (2013.01); *A61K 9/2013* (2013.01); *A61K 9/2018* (2013.01); *A61K 9/2095* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 4,844,909 A * | 7/1989 | Goldie | A61K 9/1652 424/480 |
| 5,547,943 A | 8/1996 | Iida et al. | |
| 5,567,439 A | 10/1996 | Myers et al. | |
| 5,601,839 A * | 2/1997 | Quan | A61K 9/0014 424/448 |
| 5,783,212 A | 7/1998 | Fassihi et al. | |
| 5,910,319 A | 6/1999 | Anderson et al. | |
| 6,224,909 B1 | 5/2001 | Opitz et al. | |
| 6,287,599 B1 | 9/2001 | Burnside et al. | |
| 6,485,746 B1 | 11/2002 | Campbell et al. | |
| 7,138,143 B1 | 11/2006 | Mukai et al. | |
| 7,576,135 B2 | 8/2009 | Ohta et al. | |
| 7,910,131 B2 | 3/2011 | Bhatt et al. | |
| 8,765,178 B2 | 7/2014 | Parikh et al. | |
| 2001/0006649 A1 | 7/2001 | Chen | |
| 2002/0054911 A1 | 5/2002 | Oh | |
| 2003/0035836 A1 | 2/2003 | Shanghvi et al. | |
| 2003/0198670 A1 | 10/2003 | Kumbhani et al. | |
| 2004/0052844 A1 | 3/2004 | Hsiao et al. | |
| 2004/0151772 A1 | 8/2004 | Andersen et al. | |
| 2005/0020645 A1 | 1/2005 | Ohta et al. | |
| 2005/0096365 A1 | 5/2005 | Fikstad et al. | |
| 2005/0118266 A1 | 6/2005 | Khan et al. | |
| 2005/0119486 A1 | 6/2005 | Ohta et al. | |
| 2005/0169994 A1 | 8/2005 | Burke et al. | |
| 2005/0245565 A1 | 11/2005 | Ohta et al. | |
| 2005/0276851 A1 | 12/2005 | Cunningham et al. | |
| 2006/0008418 A1 | 1/2006 | Hansen et al. | |
| 2006/0039974 A1 | 2/2006 | Akiyama et al. | |
| 2006/0159753 A1 | 7/2006 | Ueki et al. | |
| 2006/0280789 A1 | 12/2006 | Ueki et al. | |
| 2007/0026062 A1 | 2/2007 | Holm et al. | |
| 2007/0098843 A1 | 5/2007 | Tomohira | |
| 2007/0224129 A1 | 9/2007 | Guimberteau et al. | |

(Continued)

FOREIGN PATENT DOCUMENTS

| | | |
|---|---|---|
| EP | 1 291 014 A1 | 3/2002 |
| EP | 1 970 052 A2 | 9/2008 |
| EP | 2 105 133 A1 | 9/2009 |
| EP | 2 140 867 A1 | 1/2010 |
| JP | 63107933 A | 5/1988 |
| JP | 10330253 A | 12/1998 |
| JP | 2001513752 A | 9/2001 |
| JP | 20011270821 A | 10/2001 |
| JP | 2001522794 A | 11/2001 |
| JP | 2001524131 A | 11/2001 |

(Continued)

OTHER PUBLICATIONS

Goforth, H.W., "Hydromorphone-OROS Formulation," Expert Opinion on Pharmacotherapy 11(7):1207-1214, May 2010.
International Search Report and Written Opinion dated Oct. 29, 2013, issued in corresponding International Application No. PCT/JP2013/073519, filed Sep. 2, 2013, 6 pages.

(Continued)

*Primary Examiner* — Jennifer A Berrios
(74) *Attorney, Agent, or Firm* — Christensen O'Connor Johnson Kindness PLLC; George Renzoni; Juan Zheng (57) ABSTRACT

An object is to provide a hydromorphone hydrochloride- or oxycodone hydrochloride hydrate-containing sustained-release pharmaceutical composition for oral administration that reliably exhibits its main pharmacological effect and has excellent formulation stability that avoids dose dumping of the principal drug, such as alcohol resistance. The present invention provides a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein the content ratio of the component (C) to the component (B) by weight in the composition, (C)/(B), is 11/3 to 3/11.

27 Claims, 4 Drawing Sheets

(56) References Cited

U.S. PATENT DOCUMENTS

| | | |
|---|---|---|
| 2008/0004260 A1 | 1/2008 | Singh |
| 2008/0089937 A1 | 4/2008 | Gan et al. |
| 2008/0181947 A1 | 7/2008 | Kojima et al. |
| 2008/0187588 A1 | 8/2008 | Zuleger et al. |
| 2008/0260815 A1 | 10/2008 | Hayes et al. |
| 2008/0268046 A1 | 10/2008 | Zuleger et al. |
| 2008/0274180 A1 | 11/2008 | Jathar et al. |
| 2009/0099151 A1 | 4/2009 | Jain et al. |
| 2009/0105491 A1 | 4/2009 | Sato et al. |
| 2009/0221621 A1 | 9/2009 | Sathyan et al. |
| 2010/0145053 A1 | 6/2010 | Patel et al. |
| 2011/0091537 A1 | 4/2011 | Castan |
| 2013/0004550 A1 | 1/2013 | Kanamaru |
| 2013/0005763 A1 | 1/2013 | Kanamaru et al. |
| 2013/0012535 A1 | 1/2013 | Kanamaru et al. |

FOREIGN PATENT DOCUMENTS

| | | |
|---|---|---|
| JP | 2003507413 A | 2/2003 |
| JP | 2004026750 A | 1/2004 |
| JP | 2004518676 A | 6/2004 |
| JP | 2006507216 A | 3/2006 |
| JP | 2007537175 A | 12/2007 |
| JP | 2007537183 A | 12/2007 |
| JP | 2008169173 A | 7/2008 |
| JP | 2009500317 A | 1/2009 |
| JP | 2009532462 A | 9/2009 |
| JP | 2009535351 A | 10/2009 |
| RU | 2009105373 A | 2/2009 |
| WO | 2001023000 A1 | 4/2001 |
| WO | 2003000657 A1 | 1/2003 |
| WO | 2003000680 A1 | 1/2003 |
| WO | 2003016302 A1 | 2/2003 |
| WO | 03/074033 A1 | 9/2003 |
| WO | 2004058715 A1 | 7/2004 |
| WO | 2005000312 A1 | 1/2005 |
| WO | 2005048979 A2 | 6/2005 |
| WO | 2006070781 A1 | 7/2006 |
| WO | 2008041553 A1 | 4/2008 |
| WO | 2008100107 A1 | 8/2008 |
| WO | 2008/129846 A1 | 10/2008 |
| WO | 2009047802 A2 | 4/2009 |
| WO | 2009057138 A2 | 5/2009 |
| WO | 2009076764 A1 | 6/2009 |
| WO | 2010/012482 A1 | 2/2010 |
| WO | 2011/045769 A2 | 4/2011 |
| WO | 2011/084593 A2 | 7/2011 |
| WO | 2011/102504 A1 | 8/2011 |
| WO | 2011/106416 A2 | 9/2011 |

OTHER PUBLICATIONS

Walden, M., et al., "The Effect of Ethanol on the Release of Opioids from Oral Prolonged-Release Preparations," Drug Development and Industrial Pharmacy 33:1101-1111, Oct. 2007.

Cheng, Y-H, et al., "Schizophrenia and Drug Delivery Systems," Jounral of Drug Targeting 8(2):107-117, Jan. 2000.

Kojima, M., and H. Nakagami, "Development of Controlled Release Matrix Pellets by Annealing With Micronized Water-Insoluble or Enteric Polymers," Journal of Controlled Release 82(2-3):335-343, Aug. 2002.

Extended European Search Report dated Mar. 29, 2016, issued in corresponding European Application No. 13832279.7, filed Sep. 2, 2013, 9 pages.

Smith, H.S. "Enteral Controlled-Release Opioid Delivery Systems," Pain Medicine 10(S1):S30-S38, Apr. 2009.

Chinese Search Report dated Jan. 12, 2016, issued in corresponding Chinese Application No. 2013800573825, filed Sep. 2, 2013, 2 pages.

Official Action (RU) dated Aug. 1, 2017, issued in corresponding Russian Application No. 2015112122/15(018963), filed Sep. 2, 2013, 10 pages.

\* cited by examiner

HYDROMORPHONE HYDROCHLORIDE-CONTAINING ORAL SUSTAINED-RELEASE PHARMACEUTICAL COMPOSITION

TECHNICAL FIELD

The present invention relates to a hydromorphone hydrochloride- or oxycodone hydrochloride hydrate-containing oral sustained-release pharmaceutical composition that reliably exhibits its main pharmacological effect when orally administered once or twice a day.

BACKGROUND ART

Sustained-release preparations for the adjustment of blood concentrations of drugs are highly useful in terms of separation between the main pharmacological effect and adverse reaction, improvement in compliance (e.g., the number of doses reduced by improvement in prolonged efficacy), medical economy, etc. In this regard, some techniques have been reported for sustained-release preparations. Meanwhile, since compounds exhibiting the main pharmacological effect have diverse chemical properties, some techniques, albeit still insufficient, of formulating sustained-release preparations aimed at adapting to the diversity of these compounds have been reported (see e.g., Patent Literatures 1 and 2).

A narcotic analgesic hydromorphone (see e.g., Non-patent Literature 1) has a potent analgesic effect and exhibits an analgesic effect 3.5 times as strong as that of oxycodone and 5 times as strong as that of morphine upon oral administration, and 8 times as strong as that of morphine as injections. In addition, this drug can be administered to patients having difficulties in taking increased doses of existing drugs. For these reasons, the drug is widely used around the world and also used over a long duration. Hydromorphone and another narcotic analgesic oxycodone are known to be highly tolerated, compared with morphine, in terms of opioid-specific adverse reactions (constipation, nausea or vomiting, itching, somnolence, respiratory depression, etc.). Oxycodone is known to undergo metabolism by cytochrome CYP450 (CYP3A4 or CYP2D6) and thus care is required for its combined use with drugs that inhibit CYP3A4 or CYP2D6. On the other hand, hydromorphone inhibits cytochrome CYP450 (CYP3A4 or CYP2D6) less than oxycodone, fentanyl, and morphine and, advantageously, is unlikely to interact with drugs that are metabolized by CYP. In addition, its metabolites have no analgesic effect. Hydromorphone therefore has the following advantages: for example, the drug can be used more safely than morphine even for patients with deteriorated functions of the kidney, which serves as an excretion pathway; the drug exhibits no histamine release action; and the drug has less adverse reaction (itching) than that of morphine.

In cancer treatment, pain management is very important for improving QOL of patients and also makes up a significant portion of the treatment. Hydromorphone or oxycodone is a typical drug used overseas in opioid rotation for cancer pain and probably makes a great contribution as a standard drug to control pain for patients.

In general, a problem in the design of sustained-release preparations for oral administration is dose dumping of the drug when the sustained-release preparation collapses due to mechanical stress resulting from the presence of food in the upper gastrointestinal tract, gastrointestinal motility, and so on (see Patent Literature 3). Hydromorphone or oxycodone is a basic compound and a highly water-soluble drug and is therefore easily soluble in a neutral aqueous solution such as a neutral buffer. Dose dumping of the narcotic analgesic, however, has the risk of becoming a lethal adverse reaction in some cases. A solution to the problem of dose dumping is a crucial issue for sustained-release preparations of the narcotic analgesic. According to study results, Palladone®, a previously known sustained-release preparation of the narcotic analgesic hydromorphone, was found to cause dose dumping resulting from damage to the sustained release preparation, when taken together with an alcohol (see e.g., Non-patent Literature 2). Hence, the U.S. Food and Drug Administration (FDA) requested the withdrawal of sustained-release capsules of Palladone® from the market (see the FDA press release of Jul. 13, 2005). The FDA further warned patients that they may incur deadly consequences by taking Palladone® with an alcohol beverage. Against this background, there has been a demand for an alcohol-resistant sustained-release preparation (sustained-release pharmaceutical composition) containing a narcotic analgesic such as hydromorphone or oxycodone as a principal pharmaceutically active ingredient without possible dose dumping.

CITATION LIST

Non-Patent Literature

Non-patent Literature 1: Expert Opin. Pharmacother., 2010, 11 (7), 1207-1214

Non-patent Literature 2: Drug Development and Industrial Pharmacy, 33: 1101-1111, 2007

Patent Literature

Patent Literature 1: Japanese Patent Application Publication No. 2006/507216

Patent Literature 2: Japanese Patent Application Publication No. 2004/518676

Patent Literature 3: International Publication No. WO 2011-102504

SUMMARY OF INVENTION

Technical Problem

An object of the present invention is to provide a sustained-release pharmaceutical composition for oral administration containing hydromorphone hydrochloride or oxycodone hydrochloride hydrate as a principal pharmaceutically active ingredient, which avoids dose dumping of the drug caused by mechanical stress and the presence of an alcohol, reliably exhibits its main pharmacological effect when orally administered once or twice a day, and has excellent stability.

Solution to Problem

The present inventors have conducted diligent studies on sustained-release pharmaceutical compositions for oral administration containing hydromorphone hydrochloride or oxycodone hydrochloride hydrate as a principal pharmaceutically active ingredient. As a result, the present inventors have found that a sustained-release pharmaceutical composition comprising (A) hydromorphone hydrochloride, or oxycodone hydrochloride hydrate, (B) hydroxypropyl methylcellulose acetate succinate (hereinafter, also abbreviated to HPMCAS) having a median size ($D_{50}$) of 40 μm or smaller, (C) a cellulose derivative, and (D) a saccharide can avoid dose dumping of the drug in the presence of an alcohol and satisfies prolonged dissolution properties. The present inventors have further found a formulation method for avoiding the formation of related substance resulting from time-dependent decomposition of hydromorphone hydrochloride in the sustained-release pharmaceutical composition during storage of the sustained-release pharmaceutical composition. On the basis of these findings, the present invention has been completed.

Specifically, the present invention provides the following (1) to (24):

(1) A sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 11/3 to 3/11.

(2) The sustained-release pharmaceutical composition according to (1), wherein the component (B) has a median size ($D_{50}$) of 20 μm or smaller.

(3) The sustained-release pharmaceutical composition according to (1), wherein the component (B) has a median size ($D_{50}$) of 10 μm or smaller and $D_{90}$ of 20 μm or smaller.

(4) The sustained-release pharmaceutical composition according to any one of (1) to (3), wherein the content of the component (B) in the composition is 5 to 75% by weight.

(5) The sustained-release pharmaceutical composition according to any one of (1) to (3), wherein the content of the component (B) in the composition is 10 to 60% by weight.

(6) The sustained-release pharmaceutical composition according to any one of (1) to (5), wherein the content of the component (A) in the composition is 0.3 to 30% by weight in terms of a free form of hydromorphone hydrochloride or in terms of an anhydrous form of oxycodone hydrochloride hydrate.

(7) The sustained-release pharmaceutical composition according to any one of (1) to (6), wherein the content of the component (C) in the composition is 5 to 75% by weight.

(8) The sustained-release pharmaceutical composition according to any one of (1) to (6), wherein the content of the component (C) in the composition is 10 to 60% by weight.

(9) The sustained-release pharmaceutical composition according to any one of (1) to (8), wherein the content ratio of the component (C) to the component (B) in the composition, (C)/(B), is 10/4 to 7/7.

(10) The sustained-release pharmaceutical composition according to any one of (1) to (9), wherein the hydroxypropyl cellulose is hydroxypropyl cellulose having a viscosity of 150 to 400 mPa·S or 1000 to 4000 mPa·S.

(11) The sustained-release pharmaceutical composition according to any one of (1) to (10), wherein the component (D) in the composition is lactose or a sugar alcohol.

(12) The sustained-release pharmaceutical composition according to (11), wherein the sugar alcohol is mannitol, xylitol, or erythritol.

(13) The sustained-release pharmaceutical composition according to any one of (1) to (12), wherein the composition is in the form of a tablet.

(14) The sustained-release pharmaceutical composition according to any one of (1) to (12) which is a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 11/3 to 3/11,
the sustained-release pharmaceutical composition being produced by the following step:
(Step): mixing the components (A), (B), (C), and (D), and an additive, followed by molding to produce the sustained-release pharmaceutical composition in the form of a tablet.

(15) The sustained-release pharmaceutical composition according to any one of (1) to (12) which is a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 11/3 to 3/11,
the sustained-release pharmaceutical composition being produced by the following two steps:
(Step 1): mixing the components (A), (B), (C), and (D), and an additive, followed by dry granulation to produce granules (granulated product), and
(Step 2): mixing the granules produced in (Step 1) and an additive, followed by molding to produce the sustained-release pharmaceutical composition in the form of a tablet.

(16) The sustained-release pharmaceutical composition according to any one of (1) to (12) which is a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 11/3 to 3/11,
the sustained-release pharmaceutical composition being produced by the following two steps:
(Step 1): mixing the components (B), (C), and (D) to produce granules (granulated product), and
(Step 2): mixing the granules (granulated product) produced in (Step 1), the components (A) and (D), and an additive, followed by molding to produce the sustained-release pharmaceutical composition in the form of a tablet.

(17) The sustained-release pharmaceutical composition according to any one of (14) to (16), wherein the additive is a lubricant.

(18) The sustained-release pharmaceutical composition according to (17), wherein the lubricant is sodium stearyl fumarate or magnesium stearate.

(19) A method for producing the sustained-release pharmaceutical composition according to any one of (1) to (12) which is a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein the content ratio of the component (C) to the component (B) by weight in the composition, (C)/(B), is 11/3 to 3/11,
the production method comprising the following step:
(Step): mixing the components (A), (B), (C), and (D), and an additive, followed by molding to produce the sustained-release pharmaceutical composition in the form of a tablet.
(20) A method for producing the sustained-release pharmaceutical composition according to any one of (1) to (12) which is a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 11/3 to 3/11,
the production method comprising the following two steps:
(Step 1): mixing the components (A), (B), (C), and (D), and an additive, followed by dry granulation to produce granules (granulated product), and
(Step 2): mixing the granules produced in (Step 1) and an additive, followed by molding to produce the sustained-release pharmaceutical composition in the form of a tablet.
(21) A method for producing the sustained-release pharmaceutical composition according to any one of (1) to (12) which is a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 11/3 to 3/11,
the production method comprising the following two steps:
(Step 1): mixing the components (B), (C), and (D) to produce granules (granulated product), and
(Step 2): mixing the granules (granulated product) produced in (Step 1), the components (A) and (D), and an additive, followed by molding to produce the sustained-release pharmaceutical composition in the form of a tablet.
(22) The production method according to any one of (19) to (21), wherein the additive is a lubricant.
(23) The production method according to (22), wherein the lubricant is sodium stearyl fumarate or magnesium stearate.
(24) The production method according to any one of (19) to (23), wherein the method is a method for preventing an increase in related substance.

Advantageous Effects of Invention

The present invention can provide a sustained-release pharmaceutical composition for oral administration containing hydromorphone hydrochloride or oxycodone hydrochloride hydrate as a principal pharmaceutically active ingredient. The sustained-release pharmaceutical composition of the present invention has favorable tablet strength that prevents dose dumping caused in an acidic solution, under mechanical stress, and in the presence of an alcohol, and has favorable dissolution properties in a neutral solution. Thus, the sustained-release pharmaceutical composition of the present invention is effective for maintaining prolonged dissolution (release) of hydromorphone hydrochloride or oxycodone hydrochloride hydrate contained therein from the duodenum through the small intestine to the lower gastrointestinal tract. Also, use of the production method of the present invention can prevent an increase in related substance and can provide a hydromorphone or oxycodone-containing sustained-release pharmaceutical composition excellent in stability.

DESCRIPTION OF EMBODIMENTS

Hereinafter, the present invention will be described in detail.

In the present invention, "acidic solution" means an acidic dissolution test medium used for evaluation of dissolution properties in the upper gastrointestinal tract such as the stomach. Non-limiting examples of the acidic dissolution test medium can include: the JP 1st dissolution test fluid described in the Japanese Pharmacopoeia; and USP 0.1 N hydrochloric acid, 0.01 N hydrochloric acid, and Simulated Gastric Fluid without Enzyme described in the United States Pharmacopoeia.

In the present invention, "neutral solution" means a neutral dissolution test medium used for evaluation of drug dissolution properties in the small intestine, the large intestine, or the like. Non-limiting examples of the neutral dissolution test medium can include dissolution test media (pH 6.8) such as: the JP 2nd dissolution test fluid and phosphate buffer (pH 6.8) described in the Japanese Pharmacopoeia; USP Phosphate Buffer (pH 6.8) and Simulated Intestinal Fluid without Enzyme described in the United States Pharmacopoeia; and Phosphate Buffer Solution (pH 6.8) described in the European Pharmacopoeia.

The aforementioned dissolution test medium is prepared through methods described in the corresponding pharmacopoeia or the like of each country. When the employed dissolution test medium is a buffer solution, variation of the pH of the test medium is preferably within ±0.05 of pH defined for each dissolution medium.

Examples of the paddle method using an acidic dissolution medium for evaluation of the dissolution properties of the sustained-release pharmaceutical composition of the present invention in the upper gastrointestinal tract can include a method in which a dissolution test is conducted by the paddle method at rotation rates of 50 rpm and 200 rpm at 37±0.5° C. for 2 hours in 0.1 N hydrochloric acid (900 mL). As described above, hydromorphone or oxycodone in the preparation presents the problem of dose dumping of the drug when the preparation collapses due to mechanical stress resulting from the presence of food in the upper gastrointestinal tract, gastrointestinal motility, and so on. The average percentage dissolution ratio (value at the rotation rate of 200 rpm in the paddle method/value at the rotation rate of 50 rpm in the paddle method) of hydromorphone is preferably 2.0 or lower, more preferably 1.5 or lower, after the 2-hour dissolution test under acidic conditions.

Examples of the paddle method using a neutral dissolution medium for evaluation of dissolution properties in the neutral region of the sustained-release pharmaceutical composition of the present invention can include a method in which a dissolution test is conducted by the paddle method at a rotation rate of 50 rpm at 37±0.5° C. in phosphate buffer (pH 6.8; 900 mL). The average percentage dissolution of hydromorphone or oxycodone in the dissolution test medium is preferably a dissolution rate exceeding 85% within 24 hours after the start of the dissolution test. Moreover, the sustained-release pharmaceutical composition more preferably exhibits an average percentage dissolution of hydromorphone or oxycodone of 50% or lower in 2 hours after the start of the dissolution test and higher than 85% within 24 hours after the start of the dissolution test.

The dissolution test of the sustained-release pharmaceutical composition of the present invention in the presence of an alcohol was carried out according to the paddle method using an acidic dissolution medium containing 40% ethanol. As for the dissolution of hydromorphone or oxycodone in the acidic dissolution medium containing 40% ethanol, the difference in average percentage dissolution of hydromorphone or oxycodone from the corresponding acidic dissolution medium free from ethanol can be 25% or lower and is preferably 20% or lower, more preferably 15% or lower. Moreover, the average percentage dissolution ratio (acidic dissolution medium containing 40% ethanol/acidic dissolution medium) of hydromorphone or oxycodone is preferably 2.0 or lower, more preferably 1.5 or lower, in the dissolution test medium after 2 hours.

The concentration of the drug in a solution can be measured using conditions (test medium, shaking rate, and measurement time) shown in the Examples described later. In the dissolution test, the concentration of hydromorphone or oxycodone in the dissolution test medium can be calculated using the HPLC method or the like to calculate the average percentage dissolution and dissolution time of hydromorphone or oxycodone from the solid preparation.

As used herein, "average percentage dissolution" refers to the average of percentage dissolution values obtained from at least 2, preferably 6, more preferably 12 solid preparation samples for each type of solid preparation.

Hydromorphone hydrochloride that is used as the "component (A)" according to the present invention is a compound represented by the following formula (I):

[Formula 1]

(I)

Its free form (free base) is hydromorphone (INN) represented by the following formula (Ia):

[Formula 2]

(Ia)

which is also called dihydromorphinone. The IUPAC systematic name is 17-methyl-3-hydroxy-4,5α-epoxymorphinan-6-one. Hydromorphone is a morphine derivative, and this compound is classified as a narcotic analgesic for neuropathic pain acting on opioid μ receptors.

Oxycodone hydrochloride hydrate that is used as the "component (A)" according to the present invention is oxycodone hydrochloride (INN) or oxycodone hydrochloride hydrate (JAN; Japanese Pharmacopoeia) represented by the following formula (II):

[Formula 3]

(II)

Its chemical name is (5R)-4,5-epoxy-14-hydroxy-3-methoxy-17-methylmorphinan-6-one monohydrochloride trihydrate. This compound, as with morphine, is classified as a narcotic analgesic for neuropathic pain acting on opioid μ receptors.

Its anhydrous form is represented by the following formula (IIa):

[Formula 4]

(IIa)

The "hydroxypropyl methylcellulose acetate succinate (HPMCAS) (B)" according to the present invention is known as a polymer base that exhibits pH-dependent dissolution properties used in the pharmaceutical field. pH-dependent polymer bases can be classified as enteric coating bases and gastric soluble bases. In the present invention, an enteric coating base is preferred for its function in the sustained-release preparation because an enteric coating base is hardly soluble in a pH environment such as the stomach and is gradually dissolved in a neutral pH environment such as the small intestine or the large intestine.

"HPMCAS (B)" according to the present invention is sold, for example, by Shin-Etsu Chemical Co., Ltd. as AQOAT (trade name). HPMCAS (B) is available as grades such as LF, MF, HF, LG, MG, and HG based on pH dissolution properties or particle sizes. HPMCAS of grade LF (pH≥5.5; according to Japanese Pharmaceutical Excipients) is preferred.

The particle size of HPMCAS (B) of the present invention is $D_{50}$ of 40 μm or smaller, preferably $D_{50}$ of 20 μm or smaller, more preferably $D_{50}$ of 10 μm or smaller, in terms of its average particle size (median size). Moreover, its 90% cumulative particle size $D_{90}$ at which the cumulative fraction of the particles is 90% is preferably 20 μm or smaller. When HPMCAS is used, the amount of HPMCAS added is preferably 5 to 75% by weight, more preferably 10 to 60% by weight, of the composition.

The "hydroxypropyl cellulose (HPC) (C)" that can be used in the present invention is commercially available. According to, for example, the catalog of Nippon Soda Co., Ltd., two types differing in particle size can be obtained: a common product (40-mesh sieve passing rate of 99%, 400 microns or smaller) and a fine powder (100-mesh sieve passing rate of 99%, 150 microns or smaller). The common product is suitable for wet granulation, while the fine powder is suitable for direct compression or dry granulation. Available viscosity grades of HPC [viscosity value (mPa·S) at HPC concentration of 2% and 20° C.] for each particle size are SSL (2.0 to 2.9), SL (3.0 to 5.9), L (6.0 to 10), M (150 to 400), and H (1000 to 4000) in ascending order of viscosity.

The "hydroxypropyl cellulose (hereinafter, also abbreviated to HPC) (C)" preferably has a particle size corresponding to the fine powder (100-mesh sieve passing rate of 99%, 150 microns or smaller) and a viscosity corresponding to grade M (150 to 400 mPa·S) or H (1000 to 4000 mPa·S). Also, HPC may be used as a binder for the sustained-release pharmaceutical composition of the present invention. When HPC is used as a binder, this HPC is usually dissolved in water or an organic solvent such as an alcohol and used as a solution. In this case, a particle size corresponding to the common product is acceptable for the hydroxypropyl cellulose, and its viscosity is preferably one corresponding to grades L (6.0 to 10.0), SL (3.0 to 5.9), and SSL (2.0 to 2.9), more preferably grade SL (3.0 to 5.9).

The "saccharide (D)" according to the present invention is preferably lactose or a sugar alcohol.

The lactose of the present invention encompasses all lactose hydrates and lactose anhydrides. A lactose hydrate is preferred. The sugar alcohol is preferably mannitol, xylitol, and erythritol, particularly preferably mannitol.

The sustained-release pharmaceutical composition of the present invention is a sustained-release pharmaceutical composition comprising (A) hydromorphone hydrochloride or oxycodone hydrochloride hydrate, (B) HPMCAS having a median size ($D_{50}$) of 40 μm or smaller, (C) hydroxypropyl cellulose (HPC), and (D) a saccharide, wherein the content ratio of the component (C) to the component (B) by weight in the composition, (C)/(B), is 11/3 to 3/11. The sustained-release pharmaceutical composition of the present invention may further contain an excipient, a disintegrant, a binder, a fluidizing agent, a lubricant, a coloring agent, a polishing agent, etc., so long as the effects of the present invention are not impaired.

Examples of the excipient according to the present invention include: sugar derivatives such as lactose, sucrose, glucose, mannitol, and sorbitol; starch derivatives such as corn starch, potato starch, gelatinized starch, dextrin, carboxymethyl starch, and sodium carboxymethyl starch; pregelatinized starch; cellulose derivatives such as crystalline cellulose, methyl cellulose, hydroxypropyl cellulose, low-substituted hydroxypropyl cellulose, hydroxypropyl methylcellulose, carmellose, carmellose calcium, croscarmellose, and sodium croscarmellose; gum arabic; dextran; pullulan; silicate derivatives such as light anhydrous silicic acid, calcium silicate, silicic acid hydrate, synthetic aluminum silicate, and magnesium aluminometasilicate; phosphate derivatives such as dicalcium phosphate; chloride derivatives such as sodium chloride; carbonate derivatives such as calcium carbonate; sulfate derivatives such as calcium sulfate; and mixtures thereof.

Examples of the disintegrant according to the present invention include adipic acid, alginic acid, gelatinized starch, sodium carboxymethyl starch, hydrous silicon dioxide, calcium citrate, light anhydrous silicic acid, synthetic aluminum silicate, wheat starch, rice starch, calcium stearate, corn starch, tragacanth powder, potato starch, hydroxypropyl starch, pregelatinized starch, monosodium fumarate, anhydrous citric acid, and calcium dihydrogenphosphate.

Examples of the binder according to the present invention include maltose syrup powder, gum arabic, gum arabic powder, sodium alginate, propylene glycol alginate ester, hydrolyzed gelatin powder, hydrolyzed starch-light anhydrous silicic acid, fructose, hydrous silicon dioxide, agar powder, light anhydrous silicic acid, synthetic aluminum silicate, wheat flour, wheat starch, rice flour, rice starch, polyvinyl acetate resin, cellulose acetate phthalate, dioctyl sodium sulfosuccinate, dihydroxyaluminum aminoacetate, sodium potassium tartrate, water, sucrose fatty acid ester, purified gelatin, gelatin, D-sorbitol, dextrin, starch, corn starch, tragacanth, tragacanth powder, concentrated glycerin, potato starch, hydroxypropyl starch, vinylpyrrolidone-vinyl acetate copolymers, piperonyl butoxide, glucose, pregelatinized starch, pullulan, polyvinyl alcohol (completely saponified product), polyvinyl alcohol (partially saponified product), sodium polyphosphate, hydroxypropyl cellulose, and hydroxypropyl methylcellulose.

Examples of the fluidizing agent according to the present invention can include hydrous silicon dioxide, light anhydrous silicic acid, synthetic aluminum silicate, titanium oxide, stearic acid, calcium stearate, magnesium stearate, calcium tertiary phosphate, talc, corn starch, and magnesium aluminometasilicate.

Examples of the lubricant according to the present invention include cocoa fat, carnauba wax, hydrous silicon dioxide, dry aluminum hydroxide gel, glycerin fatty acid ester, magnesium silicate, light anhydrous silicic acid, hardened oil, synthetic aluminum silicate, white beeswax, magnesium oxide, sodium potassium tartrate, sucrose fatty acid ester, stearic acid, calcium stearate, magnesium stearate, stearyl alcohol, polyoxyl 40 stearate, cetanol, soybean hardened oil, gelatin, talc, magnesium carbonate, precipitated calcium carbonate, corn starch, potato starch, stearyl sodium fumarate, beeswax, magnesium metasilicate aluminate, sodium laurate, and magnesium sulfate.

Examples of the coating base according to the present invention include sugar coating bases, water-soluble film coating bases, enteric film coating bases, and sustained-release film coating bases. Sucrose is used as a sugar-coating base. Alternatively, one or two or more sugar-coating bases selected from talc, precipitated calcium carbonate, calcium phosphate, calcium sulfate, gelatin, gum arabic, polyvinylpyrrolidone, pullulan, etc. can be used alone or in combination. Examples of the water-soluble film coating bases include: cellulose derivatives such as hydroxypropyl cellulose, hydroxypropyl methylcellulose, hydroxyethyl cellulose, methyl hydroxyethyl cellulose, and sodium carboxymethyl cellulose; synthetic polymers such as polyvinyl acetal diethylaminoacetate, aminoalkyl methacrylate copolymers, polyvinylpyrrolidone, polyvinyl alcohol, and polyvinyl alcohol copolymers; and polysaccharides such as pullulan. Examples of the enteric film coating bases include: cellulose derivatives such as hydroxypropyl methylcellulose phthalate, hydroxypropyl methylcellulose acetate succinate, carboxymethyl ethylcellulose, and cellulose acetate phthalate; acrylic acid derivatives such as methacrylic acid copolymer L, methacrylic acid copolymer LD, and methacrylic acid copolymer S; and natural products such as shellac. Examples of the sustained-release film coating bases include: cellulose derivatives such as ethyl cellulose; and acrylic acid derivatives such as aminoalkyl methacrylate copolymer RS and ethyl acrylate-methyl methacrylate copolymer emulsions. Two or more of these coating bases may be mixed at an appropriate ratio for use. If necessary, the sustained-release pharmaceutical composition of the present invention may further contain appropriate pharmacologically acceptable additives such as plasticizers, excipients, lubricants, masking agents, coloring agents, and antiseptics.

Examples of the coloring agent according to the present invention can include yellow iron sesquioxide, iron sesquioxide, titanium oxide, orange essence, brown iron oxide, β-carotene, black iron oxide, food blue No. 1, food blue No. 2, food red No. 2, food red No. 3, food red No. 102, food yellow No. 4, and food yellow No. 5.

Examples of the polishing agent according to the present invention include carnauba wax, hardened oil, a polyvinyl acetate resin, white beeswax, titanium oxide, stearic acid, calcium stearate, polyoxyl 40 stearate, magnesium stearate, purified shellac, purified paraffin/carnauba wax mixture, cetanol, talc, colored silver foil, white shellac, paraffin, povidone, Macrogol 1500, Macrogol 4000, Macrogol 6000, beeswax, glycerin monostearate, and rosin.

No particular limitation is imposed on the dosage form of the sustained-release pharmaceutical composition of the present invention, so long as the solid preparation thereof can be orally administered to a subject. However, a tablet or granules are preferred, with a tablet being more preferred.

Hereinafter, another embodiment of the present invention will be described.

The sustained-release pharmaceutical composition of the present invention is a sustained release pharmaceutical composition comprising (A) hydromorphone hydrochloride or oxycodone hydrochloride hydrate, (B) hydroxypropyl methylcellulose acetate succinate (HPMCAS) having a median size ($D_{50}$) of 40 μm or smaller, (C) hydroxypropyl cellulose (HPC), and (D) a saccharide, wherein the content ratio of the component (C) to the component (B) by weight in the composition, (C)/(B), is 11/3 to 3/11, the sustained-release pharmaceutical composition being obtained by mixing these components and an optionally added additive, followed by molding.

The sustained-release pharmaceutical composition of the present invention can be produced by: mixing the components (A), (B), (C), and (D), and an added additive, followed by molding; mixing the components (A), (B), (C), and (D), and an added additive, followed by dry granulation to produce granules (granulated product), and molding the produced granules (granulated product) to produce a tablet; or producing granules (granulated product) from the components (B), (C), and (D), adding the components (A) and (D), and an additive to the granules (granulated product), and mixing them, followed by molding. For the molding, preferably, a lubricant is added as an additive to mixed powders or granules and mixed therewith, followed by compression molding. In this case, the lubricant is preferably sodium stearyl fumarate or magnesium stearate. The present invention also encompasses a coated form of a preparation obtained by mixing of the components (A), (B), (C), and (D), and an added additive followed by molding. A component containing the component (B) may be used in the coating.

The content of the component (A) in the sustained-release pharmaceutical composition of the present invention is preferably 0.3 to 30% by weight of "hydromorphone hydrochloride" in terms of a free form of hydromorphone (Ia) or 0.3 to 30% by weight of "oxycodone hydrochloride hydrate" in terms of an anhydrous form of oxycodone hydrochloride (IIa).

The preferred form of "HPMCAS" used as the component (B) in the sustained-release pharmaceutical composition of the present invention is as mentioned above. The grade of HPMCAS is preferably HF, MF, or LF, more preferably LF.

HPMCAS used as the component (B) in the sustained-release pharmaceutical composition of the present invention exhibits an average particle size ($D_{50}$) of 40 μm or smaller and preferably has $D_{50}$ of 20 μm or smaller, more preferably $D_{50}$ of 10 μm or smaller. Moreover, its 90% cumulative particle size $D_{90}$ at which the cumulative fraction of the particles is 90% is preferably 20 μm or smaller.

In the present specification, the term "$D_{50}$" refers to a particle size corresponding to the median value of a cumulative distribution curve determined using a laser diffraction-type meter HELOS (Japan Laser Corp.), i.e., a median size. Also, in the present specification, the term "$D_{90}$" refers to a particle size corresponding to 90% of the cumulative distribution curve determined using the HELOS. For example, $D_{90}$ of 20 μm means that 90% of the measured powders have a particle size of 20 μm or smaller and the remaining 10% have a particle size larger than 20 μm.

The content of the component (B) in the sustained-release pharmaceutical composition of the present invention is preferably 5 to 75% by weight, more preferably 10 to 60% by weight.

The "hydroxypropyl cellulose (HPC)" used as the component (C) in the sustained-release pharmaceutical composition of the present invention is preferably a fine powder (100-mesh sieve passing rate of 99%) or grade M (viscosity: 150 to 400 mPa·S) or H (viscosity: 1000 to 4000 mPa·S).

The content of the component (C) in the sustained-release pharmaceutical composition of the present invention is preferably 5 to 75% by weight, more preferably 10 to 60% by weight.

The content ratio of the component (C) to the component (B) by weight in the sustained-release pharmaceutical composition of the present invention, (C)/(B), is 11/3 to 3/11 and is preferably 10/4 to 7/7, more preferably 10/4 to 8/6.

A general package form available in medical use can be used for the preparation according to the present invention. Specifically, examples thereof include plastic bottle packages, vial packages, and PTP packages. The package form may be used in combination with a desiccant or a deoxidizer.

Examples of the desiccant can include synthetic zeolite (Shin-Etsu Kasei Kogyo Co., Ltd.). Examples of the deoxidizer can include Pharmakeep® (Mitsubishi Gas Chemical Company, Inc.).

Moreover, in the sustained-release pharmaceutical composition of the present invention, HPC is used as the component (C) and may also be used as a binder. HPC used as a binder may be a fine powder or a common product and is not limited by viscosity, so long as it can be used as a binder. Grade L (6.0 to 10.0 mPa·S), SL (3.0 to 5.9 mPa·S), SSL (2.0 to 2.9 mPa·S), or the like is preferred, with grade SL being more preferred.

The "saccharide" used as the component (D) in the sustained-release pharmaceutical composition of the present invention is preferably lactose or a sugar alcohol. The lactose may be a lactose hydrate or a lactose anhydride and is preferably a lactose hydrate. The sugar alcohol is preferably mannitol, xylitol, or erythritol, more preferably mannitol.

The content of the component (D) in the sustained-release pharmaceutical composition of the present invention is preferably 2 to 40% by weight.

The sustained-release pharmaceutical composition of the present invention may further contain an excipient, a disintegrant, a binder, a fluidizing agent, a lubricant, a coloring agent, a polishing agent, etc., so long as the effects of the present invention are not impaired.

(Method A) and (Method B) given below can be adopted as methods for producing the sustained-release pharmaceutical composition of the present invention. Hereinafter, these methods will be described.

(Method A)

The production method used is a direct compression method which involves mixing the components (A) to (D), followed by molding, or a method which involves mixing the components (A) to (D), followed by dry granulation and subsequent molding. The mixing, granulation, and molding can be performed using a method well known in the art. For the molding, preferably, a lubricant is mixed as an additive with mixed powders or granules, followed by compression molding. In this case, the lubricant is preferably sodium stearyl fumarate or magnesium stearate. The component (A) may be pulverized with a pulverizer and used. The sustained-release pharmaceutical composition of the present invention may be coated. The coated sustained-release pharmaceutical composition of the present invention can be produced by spraying of a coating solution onto molded tablets. The coating can be performed using a method well known in the art. When the preparation of the present invention contains additional additives, these additives may be added thereto in any of mixing, granulation, compression, and coating steps.

(Method B)

Another example of the preferred method for producing the preparation of the present invention can include Production Method B comprising the following two steps (Step 1) and (Step 2):

(Step 1): mixing the components (B), (C), and (D), followed by wet granulation to produce granules (granulated product), and (Step 2): adding the components (A) and (D), and an additive to the granules (granulated product) produced in (Step 1) and mixing them, followed by molding to produce a tablet. The component (A) may be pulverized with a pulverizer and used.

In this context, the mixing, wet granulation, and molding can be performed using a method well known in the art. For the molding, preferably, a lubricant is added as an additive to the granules and mixed therewith, followed by compression molding. In this case, the lubricant is preferably sodium stearyl fumarate or magnesium stearate. The sustained-release pharmaceutical composition of the present invention may be coated. The coated sustained-release pharmaceutical composition of the present invention can be produced by spraying of a coating solution onto molded tablets. The coating can be performed using a method well known in the art. When the sustained-release pharmaceutical composition of the present invention contains additional additives, these additives may be added thereto in any of mixing, granulation, compression, and coating steps.

Hereinafter, a wet granulation (fluidized-bed granulation) method (Method C) generally used will be described as a control method to be compared with the method for producing the sustained-release pharmaceutical composition of the present invention.

The components (B) to (D) are added to the component (A) and mixed therewith, followed by the wet granulation (fluidized-bed granulation) method to produce granules (granulated product). The granules (granulated product) thus produced are mixed with a lubricant as an additive, followed by molding. The component (A) may be pulverized with a pulverizer and used. The mixing, granulation, and molding can be performed using a method well known in the art.

As result of evaluating the storage stability of each of preparations produced by these production methods (Method A), (Method B), and (Method C), the preparation produced using (Method C) formed a larger level of related substance through the decomposition of hydromorphone hydrochloride than that formed by the preparation produced using (Method A) or (Method B). By contrast, no significant increase in related substance was observed in the preparations of hydromorphone hydrochloride or oxycodone hydrochloride hydrate produced in (Method A) and (Method B). Thus, the method for producing the sustained-release pharmaceutical composition of the present invention is preferably (Method A) or (Method B), particularly preferably (Method B). In this respect, (Method B) is particularly preferred because a granular mixture of the components improves the flowability of the powder and results in few variations in tablet mass. In addition, this Method B is also preferred because the narcotic component (A) is handled only in (Step 2); thus it is not required to manage the narcotic throughout the production process.

No particular limitation is imposed on the shape of the preparation of the present invention. However, a lens, disc, round, oval, almond, teardrop, or polygonal (triangle or rhombus) shape is preferred.

The sustained-release pharmaceutical composition of the present invention, which contains the components (A) to (D) and is a solid composition produced by (Method A) or (Method B), has favorable strength that can avoid dose dumping of the component (A) as a principal pharmaceutically active ingredient from the solid composition under each condition (in an acidic solution, under mechanical stress, and in the presence of an alcohol), and has favorable dissolution properties in a solution. Thus, the sustained-release pharmaceutical composition of the present invention is effective for maintenance of prolonged dissolution of hydromorphone or oxycodone of the component (A) contained therein as the principal pharmaceutically active ingredient from the duodenum through the small intestine to the lower gastrointestinal tract.

EXAMPLES

Next, the present invention will be described in detail with reference to Examples. However, the present invention is not intended to be limited to these Examples in any way.

Abbreviations used in Examples are as follows:

"HPC-SL": hydroxypropyl cellulose grade SL (manufactured by Nippon Soda Co., Ltd.)
"HPC-H": hydroxypropyl cellulose grade H (manufactured by Nippon Soda Co., Ltd.)
"HPMCAS-LF": hydroxypropyl methylcellulose acetate succinate grade LF (manufactured by Shin-Etsu Chemical Co., Ltd.)

Tests on dissolution properties in an acidic or neutral solution were conducted as follows:

(Dissolution Test in Acidic Solution)

The dissolution test was conducted by the paddle method at a rotation rate of 50 rpm at 37±0.5° C. in the JP 1st dissolution test fluid (900 mL). The time-dependent dissolution of the drug from each solid composition into the dissolution medium was measured, and the average percentage dissolution of the drug was calculated.

(Dissolution Test in Neutral Solution)

The dissolution test was conducted by the paddle method at a rotation rate of 50 rpm at 37±0.5° C. in the JP 2nd dissolution test fluid (900 mL). The time-dependent dissolution of the drug from each solid composition into the dissolution medium was measured, and the average percentage dissolution of the drug was calculated.

(Dissolution Test in Solution of pH 4.0)

The dissolution test was conducted by the paddle method at a rotation rate of 50 rpm at 37±0.5° C. in an acetate buffer of pH 4.0 (900 mL). The time-dependent dissolution of the drug from each solid composition into the dissolution medium was measured, and the average percentage dissolution of the drug was calculated.

(Dissolution Test in Acidic Solution Containing 40% Ethanol)

The dissolution test was conducted by the paddle method at a rotation rate of 50 rpm at 37±0.5° C. in the JP 1st dissolution test fluid containing 40% ethanol (900 mL). The time-dependent dissolution of the drug from each solid composition into the dissolution medium was measured, and the average percentage dissolution of the drug was calculated.

(Quantification Condition for Dissolution Test)

Detector: ultraviolet absorptiometer (measurement wavelength: 280 nm)
Column: stainless tube with an interior diameter of 4.6 mm and a length of 5 cm packed with 5 µm of an octadecylsilylated silica gel for liquid chromatography (YMC-Pack Pro C18, manufactured by YMC Co., Ltd.)
Column temperature: constant temperature around 40° C.
Mobile phase: Sodium dodecyl sulfate-containing acetic acid solution/acetonitrile mixed solution (66/34)
Flow rate: Adjusted such that the retention time of hydromorphone is approximately 3 minutes (5 mL/min)
Injection volume: 100 µL
Injector washing solution: methanol/water mixed solution (7/3)
Sample cooler temperature: 20° C.

(Related Substance Quantification Condition)

Detector: ultraviolet absorptiometer (measurement wavelength: 284 nm)
Column: stainless tube with an interior diameter of 4.6 mm and a length of 25 cm packed with 5 µm of an octadecylsilylated silica gel for liquid chromatography (Hypersil BDS C18, manufactured by Thermo Fisher Scientific K.K.)
Column temperature: room temperature
Mobile phase: Sodium dodecyl sulfate- and diethylamine-containing phosphoric acid solution (pH=3)/acetonitrile/methanol mixed solution (8/1/1)
Flow rate: Adjusted such that the retention time of hydromorphone is approximately 9 minutes (approximately 0.9 mL/min)
Injection volume: 100 µL
Injector washing solution: water/acetonitrile mixed solution (1/1)
Sample cooler temperature: 20° C.

Example 1

Production of Solid Composition [(Method A), (Method B), and (Method C)] and Storage Stability Test of Solid Composition The rate of formation of related substance was evaluated as the storage stability test of hydromorphone 2-mg tablets produced by the "direct compression method (Method A)", the "semi-direct compression method (Method B)", and the "fluidized-bed granulation method (Method C)".

<Production of Solid Composition (Table 1)>

Formulation 1 (Method A): Hydromorphone hydrochloride, mannitol, HPC-H, HPC-SL, HPMCAS-LF, and sodium stearyl fumarate were mixed and compressed using a tableting machine to produce tablets.

Formulation 2 (Method B): Mannitol, HPC-H, HPC-SL, and HPMCAS-LF were granulated using a fluidized-bed granulator, then dried, and size-regulated to obtain granules. The granules were mixed with hydromorphone hydrochloride, mannitol, and sodium stearyl fumarate and compressed using a tableting machine to produce tablets.

Formulation 3 (Method C): Hydromorphone hydrochloride, mannitol, HPC-H, HPC-SL, and HPMCAS-LF were granulated using a fluidized-bed granulator, then dried, and size-regulated to obtain granules. The granules were mixed with sodium stearyl fumarate and compressed using a tableting machine to produce tablets.

<Storage Stability Test of Solid Composition>

Related substance was quantified by the method mentioned above. The results of the storage stability test about each formulation are shown in Table 2.

TABLE 1

| Components | Composition (mg/tab) | | |
| --- | --- | --- | --- |
| | Formulation 1 (Method A) | Formulation 2 (Method B) | Formulation 3 (Method C) |
| Hydromorphone hydrochloride (as free form) | 2.26 (2) | 2.26 (2) | 2.26 (2) |
| D-Mannitol | 47.24 | 47.24 | 47.24 |
| HPC-H | 45 | 45 | 45 |
| HPC-SL | 4.5 | 4.5 | 4.5 |
| HPMCAS-LF | 45 | 45 | 45 |
| Sodium stearyl fumarate | 6 | 6 | 6 |
| Total | 150 | 150 | 150 |

TABLE 2

| Storage condition/storage period/container closure system | Related substance (total amount) (%) | | |
|---|---|---|---|
| | Formulation 1 (Method A) | Formulation 2 (Method B) | Formulation 3 (Method C) |
| Initial | 0.45 | 0.42 | 0.50 |
| 40° C. 75% RH/2 W/plastic bottle | N.T. | 0.48 | 1.07 |
| 40° C. 75% RH/1 M/plastic bottle | N.T. | 0.40 | 2.35 |
| 60° C./2 W/plastic bottle | 0.55 | 0.93 | 3.58 |

N.T.: Not Tested

<Test Results>

As for tablet stability, a significant increase in related substance was observed in the tablets of formulation 3 compared with the tablets of formulations 1 and 2.

Example 2

Dissolution Test of Hydromorphone 2-Mg and 24-Mg Tablets Produced by Semi-Direct Compression Method (Method B) and Stability Test of 2-Mg Tablet <Production of Solid Composition (Table 3)>
Formulations 4 and 5 "semi-direct compression method (Method B)": Mannitol, HPC-H, HPC-SL, and HPM-CAS-LF were mixed, then granulated using a fluidized-bed granulator, dried, and size-regulated to obtain granules. The obtained granules were supplemented and mixed with hydromorphone hydrochloride, mannitol, and sodium stearyl fumarate and compressed using a tableting machine to produce tablets.

<Test on Dissolution Properties in Each Test Medium and Storage Stability Test>

Figure 1A:
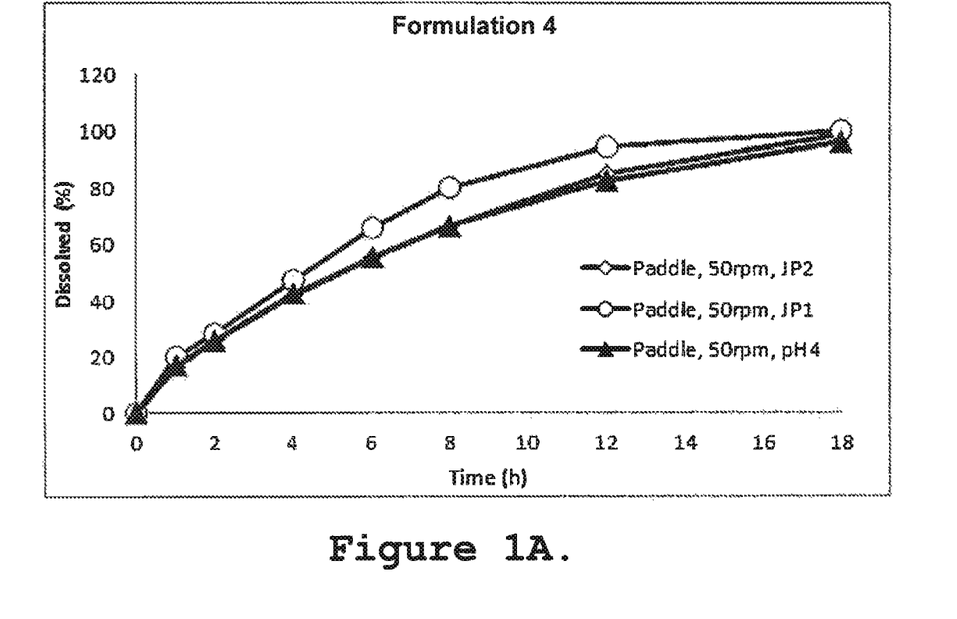
FIGS. 1A and 1B are diagrams showing the time-dependent dissolution of a drug (A) from each of solid preparations of formulations 4 (1A) and 5 (1B) produced in Example 2 into each test medium.
Figure 1B:
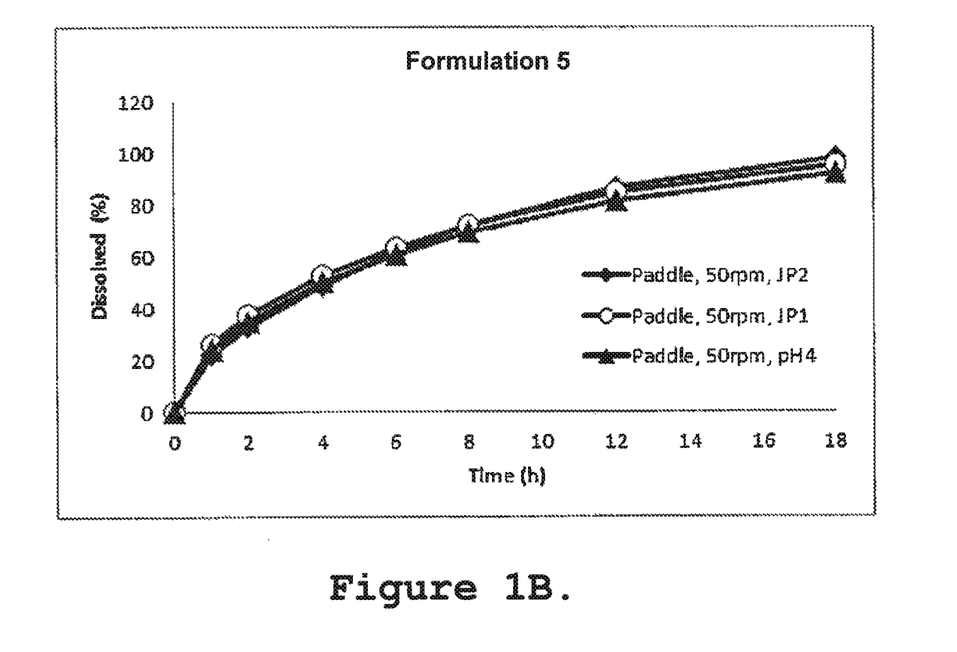

The dissolution test in each test medium and the quantification of related substance were performed by the methods mentioned above. The results of the test on dissolution properties in each test medium are shown in FIG. 1. The results of the storage stability test are shown in Table 4.

TABLE 3

| | Composition (mg/tab) | |
|---|---|---|
| Components | Formulation 4: 2-mg tablet | Formulation 5: 24-mg tablet |
| D-Mannitol | 27.75 | 41.63 |
| HPC-H | 70 | 105 |
| HPMCAS-LF | 70 | 105 |
| HPC-SL | 6 | 9 |
| D-Mannitol | 15.99 | 0 |
| Hydromorphone hydrochloride (as free form) | 2.26 (2) | 27.07 (24) |
| Sodium stearyl fumarate | 8 | 12 |
| Total | 200 | 300 |

TABLE 4

Results of stability test about formulation 4 (2-mg tablet)

| Storage condition/storage period/container closure system | Related substance (total amount) (%) |
|---|---|
| Initial | 0.42 |
| 40° C. 75% RH/3 M/plastic bottle | 0.50 |
| 40° C. 75% RH/3 M/vial | 0.37 |
| 40° C. 75% RH/3 M/PTP | 0.54 |

<Test Results>

The dissolution behaviors from the tablets of formulations 4 and 5 exhibited sustained-release profiles at all of pHs. No significant increase in related substance was observed in the stability test of the tablets of formulation 4, and the tablets of formulation 4 exhibited favorable stability.

Example 3

Influence of Alcohol on Dissolution Behavior of Hydromorphone Hydrochloride

<Method for Producing Solid Composition (Table 5)>
Formulations 6 and 7 "semi-direct compression method (Method B)": Mannitol, HPC-H, HPC-SL, and HPM-CAS-LF were mixed, then granulated using a fluidized-bed granulator, dried, and size-regulated to obtain granules. The obtained granules were supplemented and mixed with hydromorphone hydrochloride, mannitol, and sodium stearyl fumarate and compressed using a tableting machine molding to produce tablets.

<Test on Dissolution Properties in Alcohol-Supplemented and Non-Supplemented Test Media>

Figure 2A:
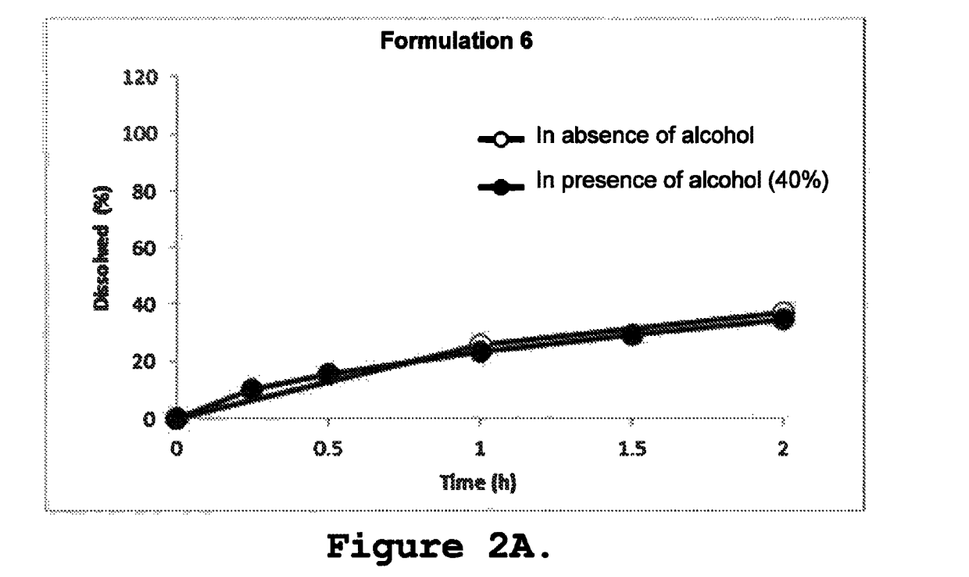
FIGS. 2A and 2B are diagrams showing the time-dependent dissolution of a drug (A) from each of solid preparations (tablets) of formulations 6 (2A) and 7 (2B) produced in Example 3 into alcohol-supplemented and non-supplemented test media.
Figure 2B:
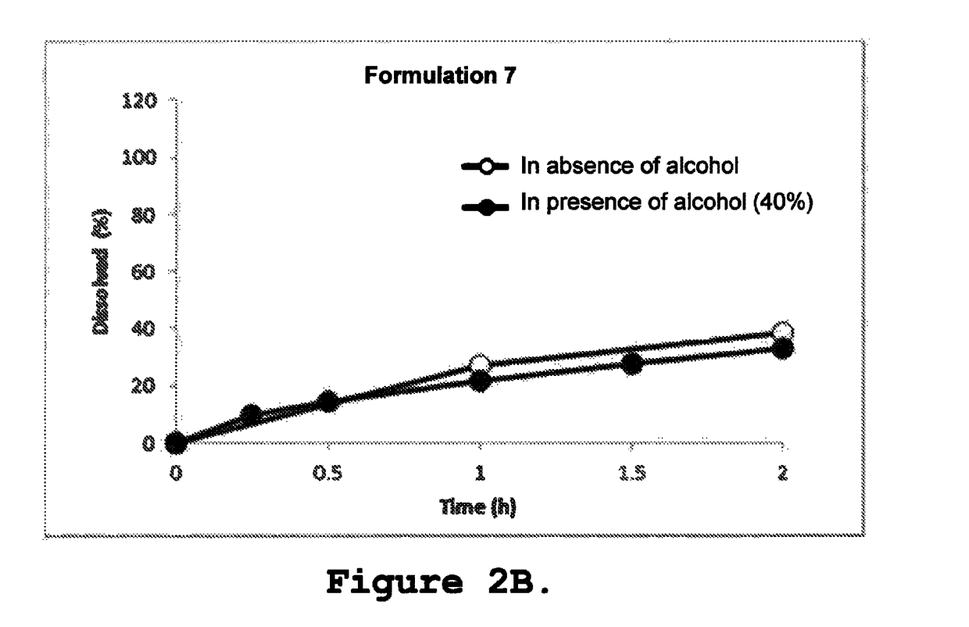

The dissolution test in an alcohol-supplemented test medium was conducted by the method mentioned above. The results of the dissolution test are shown in FIG. 2.

TABLE 5

| | Composition (mg/tab) | |
|---|---|---|
| Components | Formulation 6: 6-mg tablet | Formulation 7: 24-mg tablet |
| D-Mannitol | 14 | 21 |
| HPC-H | 82 | 123 |
| HPMCAS-LF | 58 | 87 |
| HPC-SL | 6 | 9 |
| D-Mannitol | 25.23 | 20.93 |
| Hydromorphone hydrochloride (as free form) | 6.767 (6) | 27.07 (24) |
| Sodium stearyl fumarate | 8 | 12 |
| Total | 200 | 300 |

<Test Results>

The dissolution behaviors from the tablets of formulations 6 and 7 did not significantly differ between in the presence of and in the absence of the alcohol and maintained sustained-release profiles.

Example 4

Ratio Between HPC and HPMCAS

<Method for Producing Solid Composition (Table 6)>
Formulations 8, 9, and 10 "semi-direct compression method (Method B)": Mannitol, HPC-H, HPC-SL, and HPM-CAS-LF were mixed, then granulated using a fluidized-bed granulator, dried, and size-regulated to obtain granules. The obtained granules were supplemented and mixed with hydromorphone hydrochloride, mannitol, and sodium stearyl fumarate and compressed using a tableting machine molding to produce tablets.

<Test on Dissolution Properties in Neutral Test Medium and Storage Stability Test>

Figure 3:
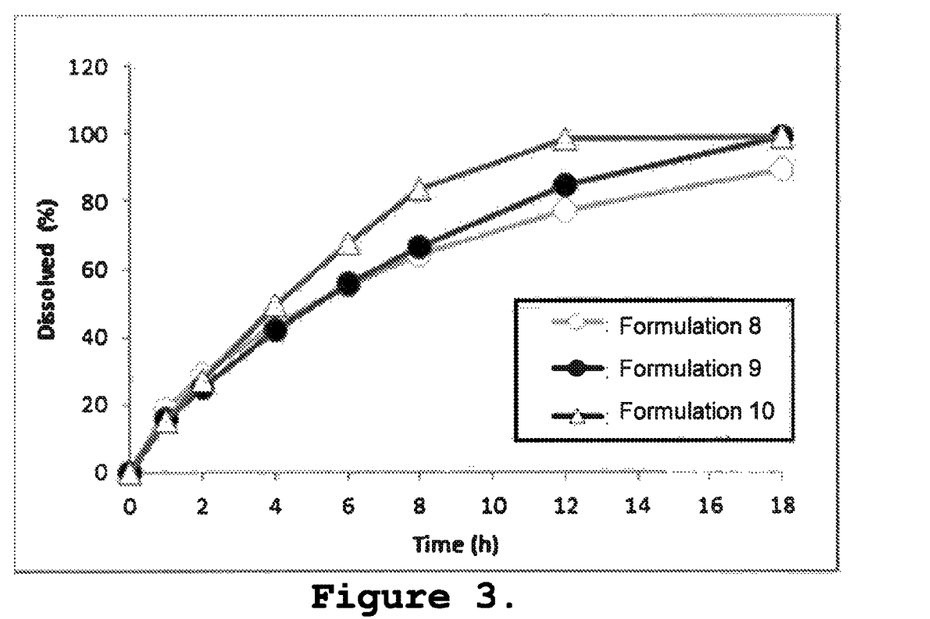
FIG. 3 is a diagram showing the time-dependent dissolution of a drug (A) from each of solid preparations (tablets) of formulations 8, 9, and 10 produced in Example 4 into a test medium (pH 6.8, 900 mL, 37° C., a paddle rotation rate of 50 rpm).

The results of the dissolution test about formulations 8, 9, and 10 are shown in FIG. 3. The results of the storage stability test are shown in Table 7.

TABLE 6

| | Composition (mg/tab) | | |
|---|---|---|---|
| Components | Formulation 8 HPC:HPMCAS = 11:3 | Formulation 9 HPC:HPMCAS = 7:7 | Formulation 10 HPC:HPMCAS = 3:11 |
| Hydromorphone hydrochloride (as free form) | 2.26 (2) | 2.26 (2) | 2.26 (2) |
| D-Mannitol | 43.744 | 43.744 | 43.744 |
| HPC-H | 110 | 70 | 30 |
| HPC-SL | 6 | 6 | 6 |
| HPMCAS-LF | 30 | 70 | 110 |
| Sodium stearyl fumarate | 8 | 8 | 8 |
| Total | 200 | 200 | 200 |

TABLE 7

Results of stability test about formulations 8, 9, and 10

| Storage condition/storage period/container closure system | Related substance (total amount) (%) | | |
|---|---|---|---|
| | Formulation 8 | Formulation 9 | Formulation 10 |
| Initial | 0.37 | 0.26 | 0.38 |
| 60° C./2 W/plastic bottle* | 0.34 | 0.27 | 0.34 |

*In the presence of a deoxidizer

<Test Results>

The dissolution behaviors from the tablets of formulations 8, 9, and 10 exhibited sustained-release profiles. In the stability test, no significant increase in related substance was observed in any of the formulations, and the tablets of these formulations exhibited favorable stability.

Example 5

Dissolution Test and Stability Test of Oxycodone Hydrochloride 5-Mg Tablet Produced by Semi-Direct Compression Method <Production of Solid Composition (Table 8)>

Formulation 11 "semi-direct compression method (Method B)": Mannitol, HPC-H, HPC-SL, and HPMCAS-LF were mixed, then granulated using a fluidized-bed granulator, dried, and size-regulated to obtain granules. The obtained granules were supplemented and mixed with oxycodone hydrochloride hydrate, mannitol, and magnesium stearate and compressed using a tableting machine to produce tablets.

<Test on Dissolution Properties in Each Test Medium and Storage Stability Test>

Figure 4:
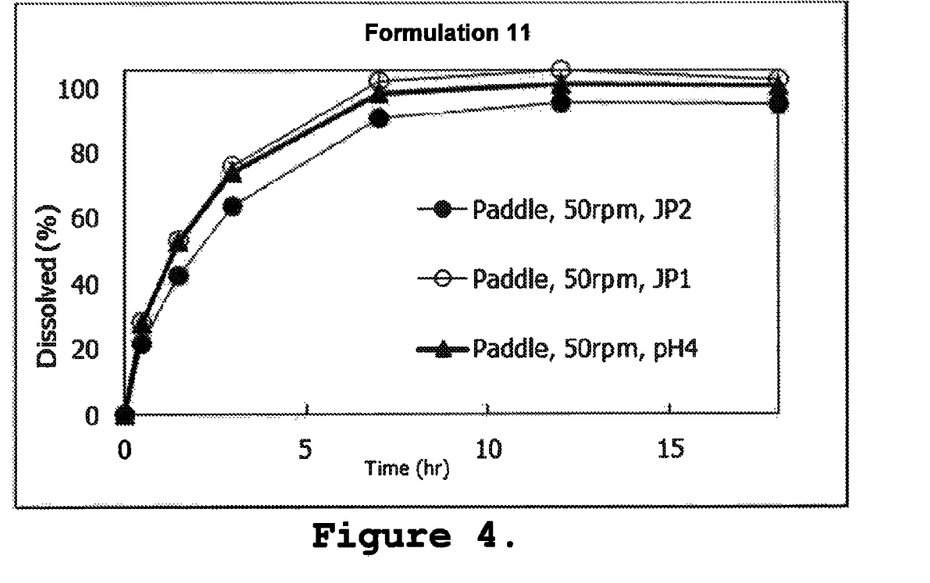
FIG. 4 is a diagram showing the time-dependent dissolution of a drug (A) from a solid preparation of formulation 11 produced in Example 5 into each test medium.

The dissolution test in each test medium and the quantification of related substance were performed by the methods mentioned above. The results of the test on dissolution properties in each test medium are shown in FIG. 4. The results of the storage stability test are shown in Table 9.

TABLE 8

| Components | Composition (mg/tab) Formulation 11: 5-mg tablet |
|---|---|
| D-Mannitol | 27.53 |
| HPC-H | 36.9 |
| HPMCAS-LF | 26.1 |
| HPC-SL | 2.7 |
| Oxycodone hydrochloride hydrate (as anhydrous form) | 5.77 (5) |
| Magnesium stearate | 1 |
| Total | 100 |

TABLE 9

| Storage condition/storage period/container closure system | Related substance (total amount) (%) Formulation 11: 5-mg tablet |
|---|---|
| Initial | 0.12 |
| 40° C. 75% RH/1 M/PTP* | 0.18 |
| 60° C./2 W/PTP* | 0.21 |

*PTP: PTP package

<Test Results>

The dissolution behaviors from the tablets of formulation 11 exhibited sustained-release profiles at all of pHs. In the stability test of the tablets of formulation 11, no significant increase in related substance was observed, and the tablets of formulation 11 exhibited favorable stability.

Example 6

Influence of Alcohol on Dissolution Behavior of Oxycodone Hydrochloride Hydrate

<Method for Producing Solid Composition (Table 10)>

Formulation 12 (40-mg tablet) "semi-direct compression method": Mannitol, HPC-H, HPC-SL, and HPMCAS-LF were mixed, then granulated using a fluidized-bed granulator, dried, and size-regulated to obtain granules. The obtained granules were supplemented and mixed with oxycodone hydrochloride hydrate, mannitol, and magnesium stearate and compressed using a tableting machine molding to produce tablets.

<Test on Dissolution Properties in Alcohol-Supplemented and Non-Supplemented Test Media>

Figure 5:
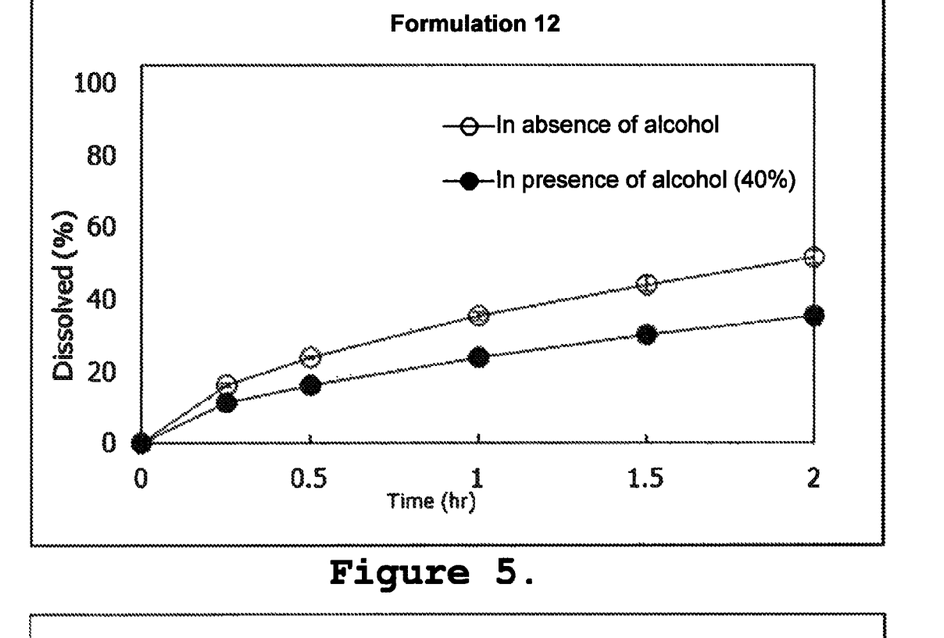
FIG. 5 is a diagram showing the time-dependent dissolution of a drug (A) from a solid preparation (tablet) of formulation 12 produced in Example 6 into alcohol-supplemented and non-supplemented test media.

The dissolution test in an alcohol-supplemented test medium was conducted by the method mentioned above. The results of the dissolution test are shown in FIG. 5.

TABLE 10

| Components | Composition (mg/tab) Formulation 12: 40-mg tablet |
|---|---|
| D-Mannitol | 20.42 |
| HPC-H | 73.8 |
| HPMCAS-LF | 52.2 |
| HPC-SL | 5.4 |
| Oxycodone hydrochloride hydrate (as anhydrous form) | 46.18 (40) |
| Magnesium stearate | 2 |
| Total | 200 |

<Test Results>
The dissolution behaviors from the tablets of formulation 12 maintained sustained-release profiles without significant acceleration of dissolution by the addition of the alcohol.

Example 7

Comparison of Dissolution Properties Between Plain Tablet and Coated Tablet

Figure 6:
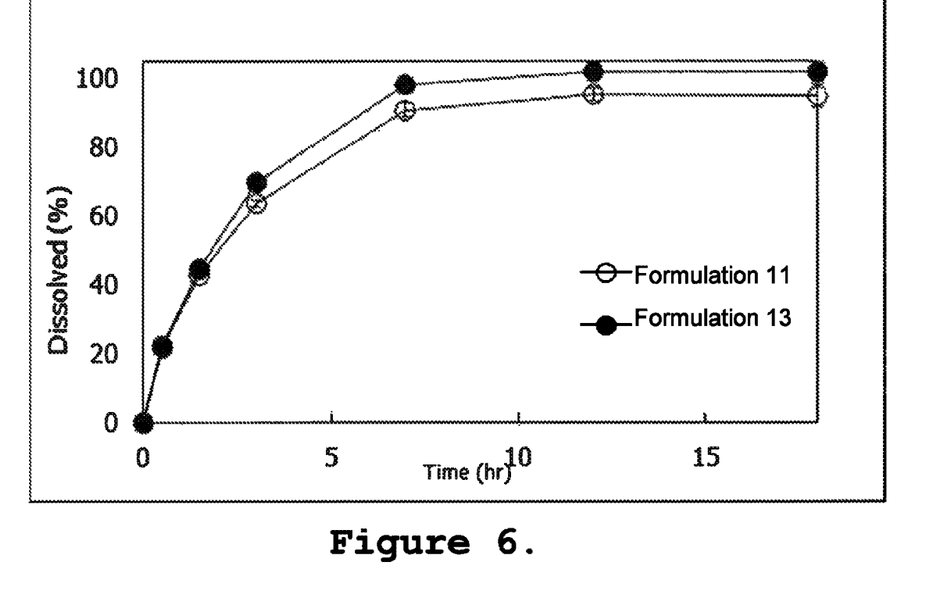
FIG. 6 is a diagram showing the time-dependent dissolution of a drug (A) from each of tablets of formulations 11 (plain tablet) and 13 (coated tablet) produced in Example 7 into each test medium.

<Method for Producing Solid Composition (Table 11)>
Formulation 11 (plain tablet) "semi-direct compression method (Method B)": Mannitol, HPC-H, HPC-SL, and HPMCAS-LF were mixed, then granulated using a fluidized-bed granulator, dried, and size-regulated to obtain granules. The obtained granules were supplemented and mixed with oxycodone hydrochloride hydrate, mannitol, and magnesium stearate and compressed using a tableting machine molding to produce tablets.
Formulation 13 (coated tablet) "semi-direct compression method (Method B)": Mannitol, HPC-H, HPC-SL, and HPMCAS-LF were mixed, then granulated using a fluidized-bed granulator, dried, and size-regulated to obtain granules. The obtained granules were supplemented and mixed with oxycodone hydrochloride hydrate, mannitol, and magnesium stearate and compressed using a tableting machine molding to produce tablets. The plain tablets were coated with OPADRY using a coating machine to produce coated tablets.
<Test on Dissolution Properties in Neutral Test Medium>
The results of the dissolution test about formulations 11 (plain tablet) and 13 (coated tablet) are shown in FIG. 6.

TABLE 11

| Components | Composition (mg/tab) | |
| --- | --- | --- |
| | Formulation 11: plain tablet | Formulation 13: coated tablet |
| D-Mannitol | 27.53 | 27.53 |
| HPC-H | 36.9 | 36.9 |
| HPMCAS-LF | 26.1 | 26.1 |
| HPC-SL | 2.7 | 2.7 |
| Oxycodone hydrochloride hydrate (as anhydrous form) | 5.77 (5) | 5.77 (5) |
| Magnesium stearate | 1 | 1 |
| OPADRY | — | 4 |
| Total | 100 | 104 |

<Test Results>
The tablets of formulations 11 (plain tablet) and 13 (coated tablet) exhibited substantially similar dissolution behaviors, both of which were sustained-release profiles of dissolution.

INDUSTRIAL APPLICABILITY

The present invention can be utilized as a sustained-release pharmaceutical composition containing hydromorphone hydrochloride or oxycodone hydrochloride hydrate and a method for producing the same.

The invention claimed is:

1. A sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 10/4 to 8/6.

2. The sustained-release pharmaceutical composition according to claim 1, wherein the component (B) has a median size ($D_{50}$) of 20 μm or smaller.

3. The sustained-release pharmaceutical composition according to claim 1, wherein the component (B) has a median size ($D_{50}$) of 10 μm or smaller and $D_{90}$ of 20 μm or smaller.

4. The sustained-release pharmaceutical composition according to claim 1, wherein the content of the component (B) in the composition is 5 to 75% by weight.

5. The sustained-release pharmaceutical composition according to claim 1, wherein the content of the component (B) in the composition is 10 to 60% by weight.

6. The sustained-release pharmaceutical composition according to claim 1, wherein the content of the component (A) in the composition is 0.3 to 30% by weight in terms of a free form of hydromorphone hydrochloride or in terms of an anhydrous form of oxycodone hydrochloride hydrate.

7. The sustained-release pharmaceutical composition according to claim 1, wherein the content of the component (C) in the composition is 5 to 75% by weight.

8. The sustained-release pharmaceutical composition according to claim 1, wherein the content of the component (C) in the composition is 10 to 60% by weight.

9. The sustained-release pharmaceutical composition according to claim 1, wherein the hydroxypropyl cellulose is hydroxypropyl cellulose having a viscosity of 150 to 400 mPa·S.

10. The sustained-release pharmaceutical composition according to claim 1, wherein the component (D) in the composition is lactose or a sugar alcohol.

11. The sustained-release pharmaceutical composition according to claim 10, wherein the sugar alcohol is mannitol, xylitol, or erythritol.

12. The sustained-release pharmaceutical composition according to claim 1, wherein the composition is in the form of a tablet.

13. A method for producing a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 10/4 to 8/6,
the production method comprising the following step:
(Step): mixing the components (A), (B), (C), and (D), and an additive, followed by molding to produce the sustained-release pharmaceutical composition in the form of a tablet.

14. A method for producing a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein
the content ratio of the component (C) to the component (B) by weight in the composition, (C)/(B), is 10/4 to 8/6,
the production method comprising the following two steps:

(Step 1): mixing the components (A), (B), (C), and (D), and an additive, followed by dry granulation to produce granules, and (Step 2): mixing the granules produced in (Step 1) and an additive, followed by molding to produce the sustained-release pharmaceutical composition in the form of a tablet.

15. A method for producing a sustained-release pharmaceutical composition comprising (A) hydromorphone hydrochloride or oxycodone hydrochloride hydrate, (B) hydroxypropyl methylcellulose acetate succinate having a median size ($D_{50}$) of 40 μm or smaller, (C) hydroxypropyl cellulose, and (D) a saccharide, wherein the content ratio of the component (C) to the component (B) by weight in the composition, (C)/(B), is 10/4 to 8/6, the production method comprising the following two steps:

(Step 1): mixing the components (B), (C), and (D) to produce granules, and (Step 2): mixing the granules produced in (Step 1), the components (A) and (D), and an additive, followed by molding to produce the sustained-release pharmaceutical composition in the form of a tablet.

16. The production method according to claim 13, wherein the additive is a lubricant.

17. The production method according to claim 16, wherein the lubricant is sodium stearyl fumarate or magnesium stearate.

18. The production method according to claim 13, wherein the method is a method for preventing an increase in related substance.

19. The production method according to claim 14, wherein the additive is a lubricant.

20. The production method according to claim 19, wherein the lubricant is sodium stearyl fumarate or magnesium stearate.

21. The production method according to claim 15, wherein the additive is a lubricant.

22. The production method according to claim 21, wherein the lubricant is sodium stearyl fumarate or magnesium stearate.

23. A sustained-release pharmaceutical composition prepared by the process of claim 13.

24. A sustained-release pharmaceutical composition prepared by the process of claim 14.

25. A sustained-release pharmaceutical composition prepared by the process of claim 15.

26. The sustained-release pharmaceutical composition of claim 1, wherein component (A) is hydromorphone hydrochloride.

27. The sustained-release pharmaceutical composition according to claim 1, wherein the hydroxypropyl cellulose is hydroxypropyl cellulose having a viscosity of 1000 to 4000 mPa·S.

\* \* \* \* \*